(12) United States Patent
Sullivan

(10) Patent No.: US 10,543,377 B2
(45) Date of Patent: *Jan. 28, 2020

(54) WEARABLE CARDIOVERTER DEFIBRILLATOR (WCD) SYSTEM MAKING SHOCK/NO SHOCK DETERMINATIONS BY AGGREGATING ASPECTS OF PATIENT PARAMETERS

(71) Applicant: West Affum Holdings Corp., Grand Cayman (KY)

(72) Inventor: Joseph L. Sullivan, Kirkland, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,816

(22) Filed: Jun. 6, 2018

(65) Prior Publication Data

US 2018/0280710 A1 Oct. 4, 2018

Related U.S. Application Data

(60) Division of application No. 15/421,165, filed on Jan. 31, 2017, now Pat. No. 10,016,614, which is a
(Continued)

(51) Int. Cl.
*A61N 1/39* (2006.01)
*A61N 1/04* (2006.01)
(Continued)

(52) U.S. Cl.
CPC ......... *A61N 1/3987* (2013.01); *A61B 5/0205* (2013.01); *A61B 5/0402* (2013.01);
(Continued)

(58) Field of Classification Search
None
See application file for complete search history.

(56) References Cited

U.S. PATENT DOCUMENTS 3,724,355 A 4/1973 Unger
4,291,699 A 9/1981 Geddes et al.
(Continued)

FOREIGN PATENT DOCUMENTS

WO 1998039061 A2 9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Kennedy Schaetzle
(74) *Attorney, Agent, or Firm* — Spectrum IP Law Group LLC

(57) ABSTRACT

In embodiments, a WCD system includes one or more transducers that may sense patient parameters from different parts of the patient's body, and thus render physiological inputs from those parameters. Individual analysis scores may be determined from the physiological inputs, and an aggregate analysis score may be determined from the individual analysis scores. A shock/no shock determination may be made depending on whether or not the aggregate analysis score meets an aggregate shock criterion. Accordingly, multiple inputs are considered in making the shock/no shock determination.

26 Claims, 9 Drawing Sheets

Related U.S. Application Data division of application No. 14/941,591, filed on Nov. 14, 2015, now Pat. No. 9,592,403, and a continuation-in-part of application No. 14/461,670, filed on Aug. 18, 2014, now abandoned, and a continuation-in-part of application No. 14/743,882, filed on Jun. 18, 2015, now abandoned, which is a continuation of application No. 14/189,789, filed on Feb. 25, 2014, now Pat. No. 9,089,685.

(60) Provisional application No. 62/165,166, filed on May 21, 2015, provisional application No. 61/769,098, filed on Feb. 25, 2013.

(51) Int. Cl.
| | |
|---|---|
| A61B 5/0205 | (2006.01) |
| A61B 5/0464 | (2006.01) |
| A61B 5/00 | (2006.01) |
| A61B 5/0402 | (2006.01) |
| A61N 1/02 | (2006.01) |
| A61B 5/0408 | (2006.01) |
| A61B 5/021 | (2006.01) |
| A61B 5/145 | (2006.01) |
| A61B 5/0472 | (2006.01) |

(52) U.S. Cl.
CPC ........ *A61B 5/0464* (2013.01); *A61B 5/04085* (2013.01); *A61B 5/6805* (2013.01); *A61N 1/02* (2013.01); *A61N 1/0484* (2013.01); *A61N 1/39* (2013.01); *A61N 1/3918* (2013.01); *A61N 1/3925* (2013.01); *A61B 5/021* (2013.01); *A61B 5/0472* (2013.01); *A61B 5/14542* (2013.01)

(56) References Cited

U.S. PATENT DOCUMENTS

| | | | |
|---|---|---|---|
| 4,583,524 A | 4/1986 | Hutchins | |
| 4,619,265 A | 10/1986 | Morgan et al. | |
| 4,895,151 A | 1/1990 | Grevis et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,425,749 A | 6/1995 | Adams | |
| 5,474,574 A | 12/1995 | Payne et al. | |
| 5,601,612 A | 2/1997 | Gliner et al. | |
| 5,630,834 A | 5/1997 | Bardy | |
| 5,662,690 A | 9/1997 | Cole et al. | |
| 5,769,872 A | 6/1998 | Lopin et al. | |
| 5,782,878 A | 7/1998 | Morgan et al. | |
| 5,792,204 A | 8/1998 | Snell | |
| 5,803,927 A | 9/1998 | Cameron et al. | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,068,651 A | 5/2000 | Brandell | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,351,671 B1 | 2/2002 | Myklebust et al. | |
| 6,356,785 B1 | 3/2002 | Snyder | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,681,003 B2 | 1/2004 | Linder et al. | |
| 6,694,187 B1 | 2/2004 | Freeman | |
| 6,762,917 B1 | 7/2004 | Verbiest et al. | |
| 6,941,168 B2 | 9/2005 | Girouard | |
| 7,065,401 B2 | 6/2006 | Worden | |
| 7,149,576 B1 | 12/2006 | Baura et al. | |
| 7,336,994 B2 | 2/2008 | Hettrick et al. | |
| 7,559,902 B2 | 7/2009 | Ting et al. | |
| 7,865,238 B2 | 1/2011 | Brink | |
| 7,870,761 B2 | 1/2011 | Valentine et al. | |
| 7,894,894 B2 | 2/2011 | Stadler et al. | |
| 7,974,689 B2 | 7/2011 | Volpe et al. | |
| 8,036,746 B2 | 10/2011 | Sanders | |
| 8,135,462 B2 | 3/2012 | Owen et al. | |
| 8,140,154 B2 | 10/2012 | Donnelly et al. | |
| 8,369,944 B2 | 2/2013 | Macho et al. | |
| 8,644,925 B2 | 2/2014 | Volpe et al. | |
| 8,825,154 B2 | 9/2014 | Jorgenson et al. | |
| 8,897,860 B2 | 11/2014 | Volpe et al. | |
| 8,965,500 B2 | 2/2015 | Macho et al. | |
| 8,996,101 B2 | 3/2015 | Zhang et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,592,403 B2 * | 3/2017 | Sullivan | A61B 5/0205 |
| 10,016,614 B2 * | 7/2018 | Sullivan | A61B 5/0205 |
| 2003/0158593 A1 | 8/2003 | Heilman et al. | |
| 2004/0220623 A1 | 11/2004 | Hess | |
| 2005/0107833 A1 | 5/2005 | Freeman et al. | |
| 2005/0107834 A1 | 5/2005 | Freeman et al. | |
| 2006/0017575 A1 | 1/2006 | McAdams | |
| 2007/0179539 A1 | 8/2007 | Degroot et al. | |
| 2008/0208070 A1 | 8/2008 | Snyder et al. | |
| 2008/0215103 A1 | 9/2008 | Powers | |
| 2008/0306560 A1 | 12/2008 | Macho | |
| 2008/0312709 A1 | 12/2008 | Volpe et al. | |
| 2009/0005827 A1 | 1/2009 | Weintraub et al. | |
| 2009/0018595 A1 | 1/2009 | Bharmi et al. | |
| 2010/0007413 A1 | 1/2010 | Herleikson | |
| 2010/0298899 A1 | 11/2010 | Donnelly et al. | |
| 2010/0331904 A1 | 12/2010 | Warren et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kalb et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0025131 A1 | 1/2014 | Sullivan et al. | |
| 2014/0025132 A1 | 1/2014 | Libbus | |
| 2014/0070957 A1 | 3/2014 | Longinotti-Buitoni et al. | |
| 2014/0150781 A1 | 6/2014 | DiCapua et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0297107 A1 | 10/2015 | Sullivan et al. | |
| 2016/0004831 A1 | 1/2016 | Carlson et al. | |

(56) References Cited

U.S. PATENT DOCUMENTS

2016/0082277 A1    3/2016  Foshee et al.
2016/0278698 A1    9/2016  Freeman et al.

OTHER PUBLICATIONS

Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Heartstart MRx and XL AED Algorithm—Application Note, Jul. 2001, Edition 2 Philips Healthcare, USA.
The LifeVest Network/Patient Data Management System, Zoll, 2015, 20C0503 Rev A.
Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

FIG. 6     *METHODS*

FIG. 9 — METHODS

WEARABLE CARDIOVERTER DEFIBRILLATOR (WCD) SYSTEM MAKING SHOCK/NO SHOCK DETERMINATIONS BY AGGREGATING ASPECTS OF PATIENT PARAMETERS

CROSS REFERENCE TO RELATED PATENT APPLICATIONS

This patent application is a divisional of U.S. patent application Ser. No. 15/421,165 filed on Jan. 31, 20172017 and issued on Jul. 10, 2018 as U.S. Pat. No. 10,016,614, which in turn is a divisional of U.S. patent application Ser. No. 14/941,591 filed on Nov. 14, 2015 and issued on Mar. 14, 2016 as U.S. Pat. No. 9,592,403, which in turn claims priority from U.S. Provisional Patent Application Ser. No. 62/165,166 filed on May 21, 2015, and which further is a Continuation-In-Part of U.S. patent application Ser. No. 14/461,670 filed on Aug. 18, 2014 and is now abandoned, and which further is a Continuation-In-Part of U.S. patent application Ser. No. 14/743,882 filed on Jun. 18, 2015 and is now abandoned, which in turn is a continuation of U.S. patent application Ser. No. 14/189,789 filed on Feb. 25, 2014 and issued on Jul. 28, 2015 as U.S. Pat. No. 9,089,685, and which in turn claimed benefit of U.S. Provisional patent application Ser. No. 61/769,098 filed on Feb. 25, 2013.

BACKGROUND

When people suffer from some types of heart arrhythmias, the result may be that blood flow to various parts of the body is reduced. Some arrhythmias may even result in a sudden cardiac arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an implantable cardioverter defibrillator ("ICD"). The ICD is surgically implanted in the chest, and continuously monitors the patient's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardioverter defibrillator ("WCD") system. (Early versions of such systems were called wearable cardiac defibrillator ("WCD") systems) A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

BRIEF SUMMARY

The present description gives instances of wearable cardioverter defibrillator ("WCD") systems, storage media that store programs, and methods, the use of which may help overcome problems and limitations of the prior art.

In embodiments, a WCD system includes one or more transducers that may sense patient parameters from different parts of the patient's body, and thus render physiological inputs from those parameters. Individual analysis scores may be determined from the physiological inputs, and an aggregate analysis score may be determined from the individual analysis scores. A shock/no shock determination may be made depending on whether or not the aggregate analysis score meets an aggregate shock criterion. An advantage over the prior art is that multiple inputs are considered in making the shock/no shock determination.

In embodiments, a WCD system includes one or more transducers that may sense patient parameters from different parts of the patient's body, and thus render physiological inputs from those parameters. First aspects and second aspects may be detected from the physiological inputs. An aggregated first aspect may be generated from the detected first aspects, and an aggregated second aspect may be generated from the detected second aspects. An aggregate analysis score may be determined from the aggregated first aspect and the aggregated second aspect. A shock/no shock determination may be made depending on whether or not the aggregate analysis score meets an aggregate shock criterion. Accordingly, such a WCD system can make shock/no shock determinations by aggregating aspects of multiple patient parameters. Accordingly, multiple inputs are considered in making the shock/no shock determination.

These and other features and advantages of this description will become more readily apparent from the Detailed Description, which proceeds with reference to the associated drawings in which:

DETAILED DESCRIPTION

As has been mentioned, the present description is about WCD systems that make shock/no shock determinations. Embodiments are now described in more detail.

A wearable cardioverter defibrillator ("WCD") system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive structure or another way for attaching to the patient, without encircling any part of the body. There can be other examples.

Figure 1:
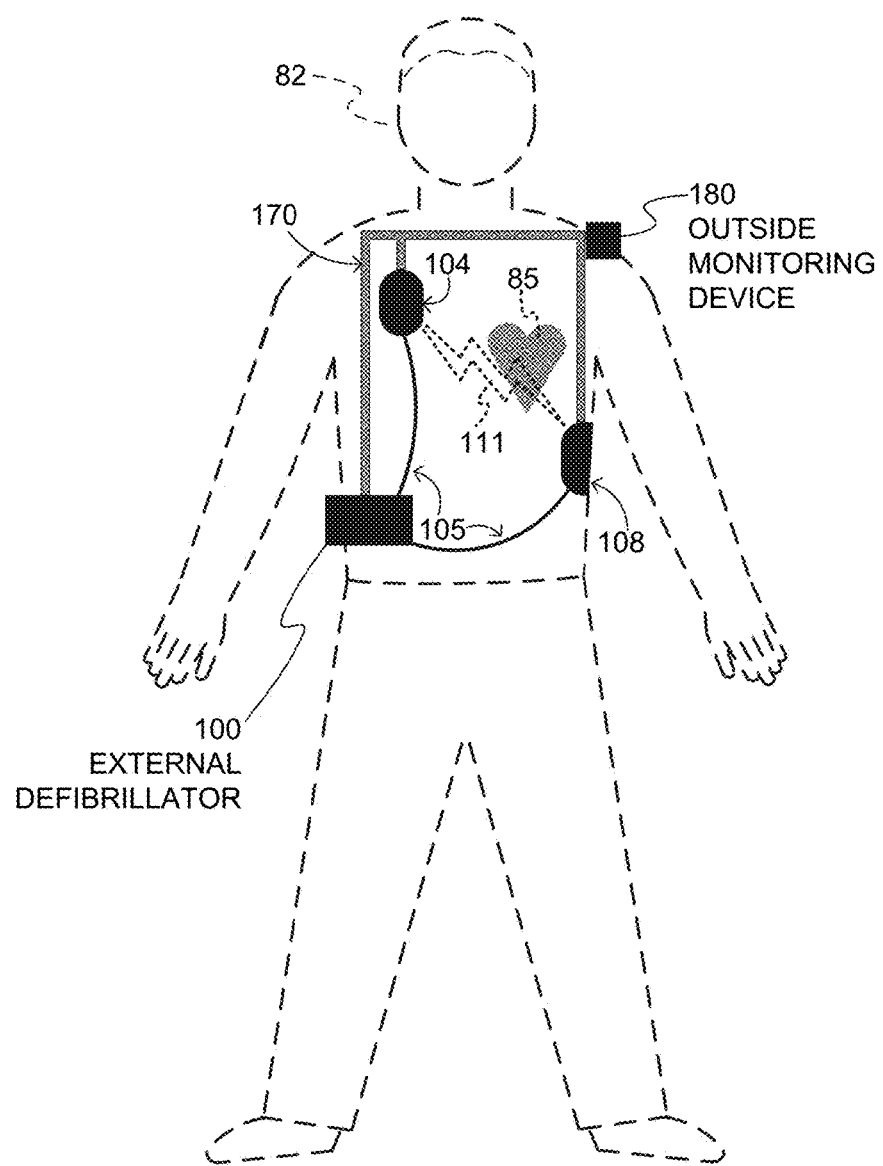
FIG. 1 is a diagram of components of a sample wearable cardioverter defibrillator ("WCD") system, made according to embodiments.

FIG. 1 depicts components of a WCD system made according to embodiments, as it might be worn by a patient 82. A patient such as patient 82 may also be referred to as a person and/or wearer, since that patient wears components of the WCD system.

In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, defibrillator 100 can defibrillate, or not defibrillate, also based on other inputs.

The WCD system may optionally include an outside monitoring device 180. Device 180 is called an "outside" device because it is provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this disclosure.

Figure 2:
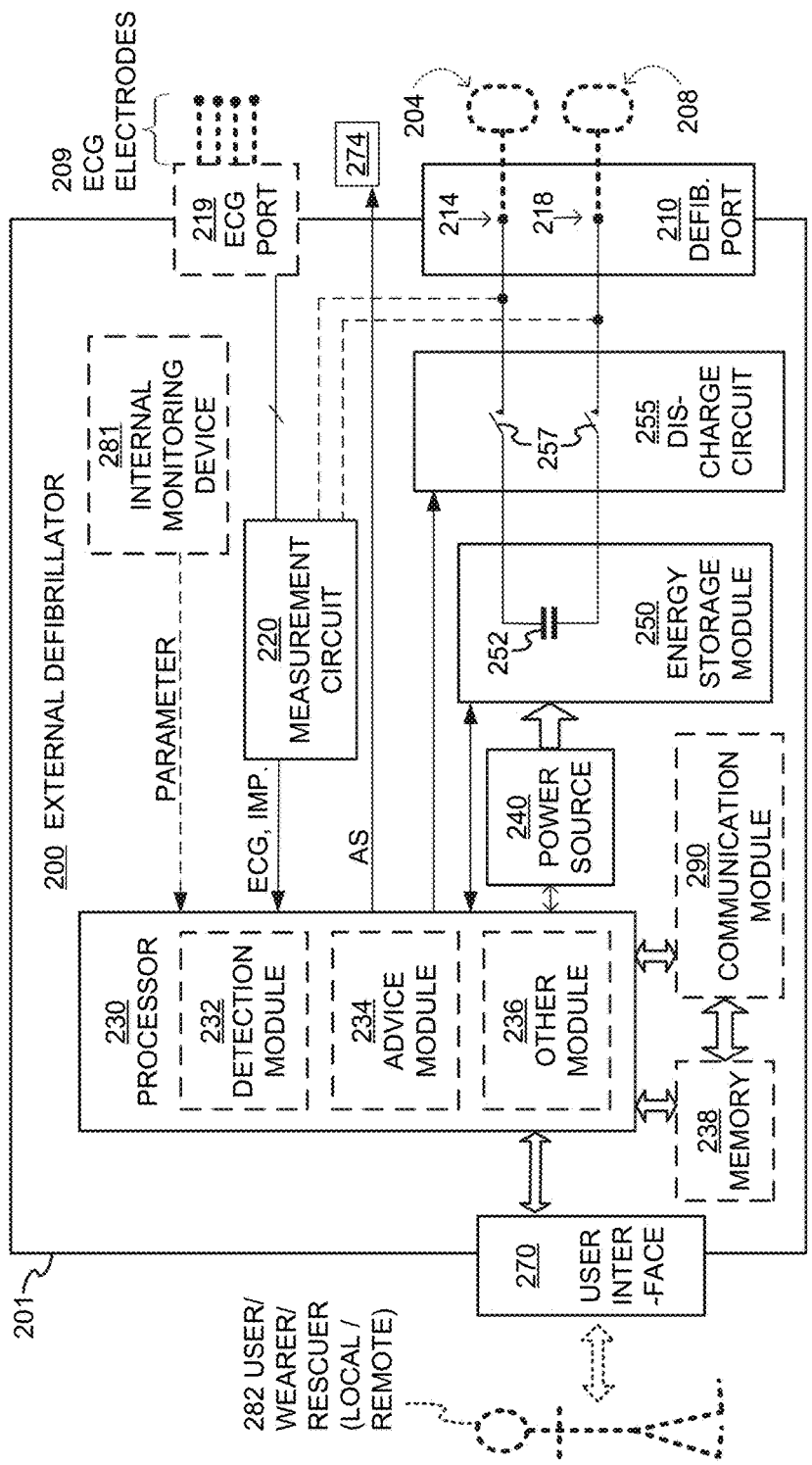
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as patient 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 270 can be made in any number of ways. User interface 270 may include output devices, which can be visual, audible or tactile, for communicating to a user. For example, an output device can be a light, or a screen to display what is sensed, detected and/or measured, and provide visual feedback to rescuer 282 for their resuscitation attempts, and so on. Another output device can be a speaker, which can be configured to issue voice prompts, etc. Sounds, images, vibrations, and anything that can be perceived by user 282 can also be called human perceptible indications. User interface 270 may also include input devices for receiving inputs from users. Such input devices may additionally include various controls, such as pushbuttons, keyboards, touchscreens, a microphone, and so on. An input device can be a cancel switch, which is sometimes called a "live-man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations. Device 281 may include one or more transducers that are configured to render one or more physiological inputs from one or more patient parameters that it senses.

Patient physiological parameters include, for example, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. Pulse detection is taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Or, one of these monitoring devices could include a location sensor such as a global positioning system ("GPS") location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, the transducer includes a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated responsive to receiving activation signal AS from processor 230, prior to the electrical discharge.

In some embodiments, defibrillator 200 also includes a transducer that includes a measurement circuit 220. Measurement circuit 220 senses one or more electrical physiological signal of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in any number of ways. Such ways include, by way of example and not of limitation, digital and/or analog processors such as microprocessors and digital signal processors ("DSP"s); controllers such as microcontrollers; software running in a machine; programmable circuits such as field programmable gate arrays ("FPGA"s), field-programmable analog arrays ("FPAA"s), programmable logic devices ("PLD"s), application specific integrated circuits ("ASIC"s), any combination of one or more of these, and so on.

Processor 230 can be considered to have a number of modules. One such module can be a detection module 232. Detection module 232 can include a ventricular fibrillation ("VF") detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a ventricular tachycardia ("VT") detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether a shock criterion is met. The determination can be made from a rhythm analysis of the captured ECG signal or otherwise.

In some embodiments, when the decision is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories ("NVM"), read-only memories ("ROM"), random access memories ("RAM"), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, processes, actions and/or methods to be performed, and/or the processor to cause other devices or components or blocks to perform such functions, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. The data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the WCD system. Module 250 is where some electrical energy is stored in the form of an electrical charge, when preparing it for discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 270.

Defibrillator 200 can optionally include a communication module 290, for establishing one or more wired or wireless communication links with other devices of other entities, such as a remote assistance center, Emergency Medical Services ("EMS"), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since bodies behave differently. For example, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

In embodiments, a WCD system includes one or more transducers that may sense patient parameters from different parts of the patient's body, and thus render physiological inputs. A shock/no shock determination may be made ultimately depending on the physiological inputs. Examples are now described.

In some embodiments, the patient parameter is one or more electrical patient physiological signals. In such embodiments, the one or more transducers may include at least three Electrocardiogram (ECG) electrodes that are configured to contact the patient. Such may be implemented in a number of ways.

Figure 3:
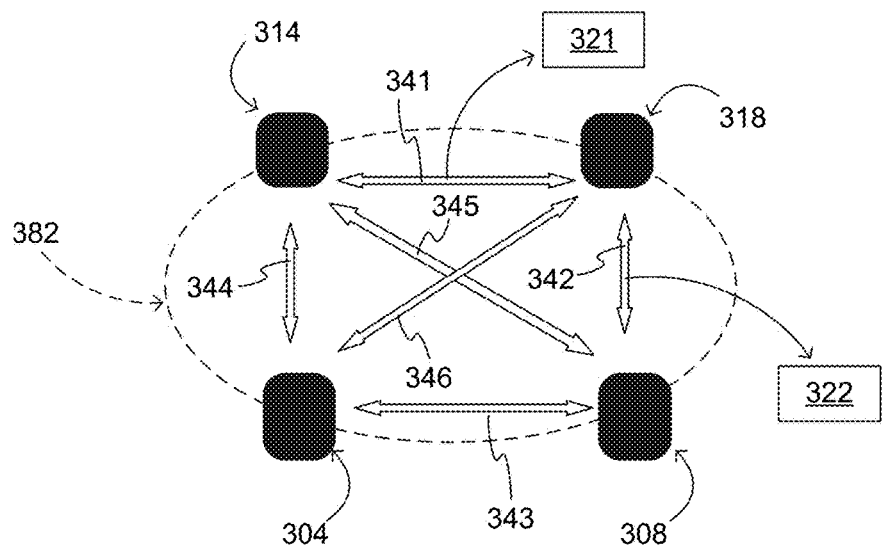
FIG. 3 is a conceptual diagram of a section of a patient's torso, to which multiple electrodes are attached according to embodiments.

For instance, FIG. 3 is a conceptual diagram of a section of a patient's torso 382. The section is parallel to the plane of the drawing. Four ECG electrodes 304, 308, 314, 318 are shown attached to torso 382. These ECG electrodes are shown with their main surfaces parallel to the plane of the drawing, but this is done only for easier recognition. In fact these main surfaces contact the skin and are perpendicular to the plane of the drawing, and could have been drawn as thick lines hugging torso 382.

It will be appreciated that ECG electrodes 304, 308, 314, 318 contact torso 382 of the patient at different places. Accordingly, when these ECG electrodes are considered in pairs, they define different vectors 341, 342, 343, 344, 345, 346 between each pair. Accordingly, the patient parameters are electrical patient physiological signals measured along these vectors. In such cases, the transducer may further include measurement circuit 220, and the physiological inputs may reflect ECG measurements measured along these vectors, or impedance measurements measured along these vectors. Only two such physiological inputs 321, 322 are shown for vectors 341, 342, so as not to clutter the drawing. When done this way, the ECG measurements along the different vectors are said to be on different respective channels.

It will be noted that, with electrodes, a large number of vectors can be had. On the other hand, a challenge with ECG measurements is ECG noise. Distinguishing the desired ECG signal from noise can be difficult. Indeed, VF is a random signal, and appears very much like noise itself. Patient movement generates noise that can interfere with ECG interpretation, and not all patient movement is voluntary. The noise problem for a WCD system may be further exacerbated by the desire to use dry, non-adhesive monitoring electrodes. Dry, non-adhesive electrodes are thought to be more comfortable for the patient to wear, but may produce more noise than a conventional ECG monitoring electrode that includes adhesive to hold the electrode in place, plus an electrolyte gel to reduce the impedance of the electrode-skin interface.

As will be understood from the below, in embodiments, a WCD system makes shock/no shock determinations from multiple patient physiological parameters. This could mean that such determinations are made either from inputs 321, 322 taken together, or even from aspects of input 321 taken multiple times.

A problem is when the different channels, from the different vectors, result in physiological inputs that give determinations that conflict with each other as to whether the patient should be shocked or not. The prior art has addressed this problem by defining one of the channels as preferred, and defaulting to it, while ignoring the rest.

In some embodiments, the patient parameter is a blood pressure of the patient. In such embodiments, the one or more transducers may include one or more blood pressure sensors, and the physiological inputs may include blood pressure measurements. Such may be implemented in a number of ways.

Figure 4:
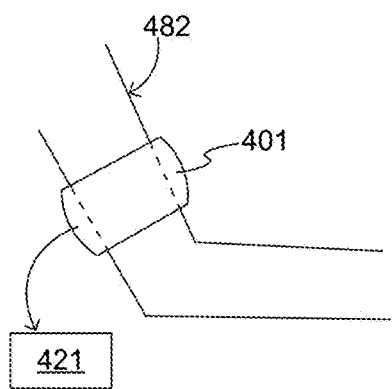
FIG. 4 is a diagram of a sample NIBP cuff applied to a patient's arm according to embodiments.

For instance, FIG. 4 is a diagram of a sample non-invasive blood pressure ("NIBP") cuff 401 according to embodiments. NIBP cuff 401 can be part of the transducer, and be part of outside monitoring device 180. In the example of FIG. 4, NIBP cuff 401 is worn on the arm 482 of the patient, even though other locations are possible. A physiological input 421 can be rendered from NIBP cuff 401. Input 421 can be one or more blood pressure measurements.

As will be understood from the below, in embodiments, a WCD system makes shock/no shock determinations from multiple patient physiological parameters. This could mean that such determinations are made either from input 421 taken multiple times, or from such inputs from multiple locations taken together. Indeed, the one or more transducers could include two blood pressure sensors that are applied to different parts of the patient's body, etc.

In some embodiments, the patient parameter is a blood oxygen saturation of the patient. In such embodiments, the one or more transducers include one or more pulse oximeters that sense blood oxygen saturation, and the physiological inputs may include blood oxygen saturation measurements. Such may be implemented in a number of ways.

Figure 5:
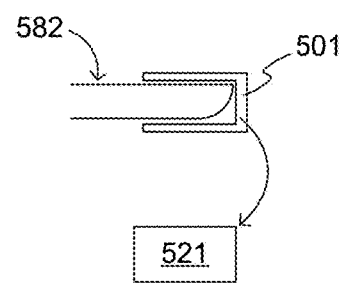
FIG. 5 is a diagram of a sample pulse oximeter applied to a patient's finger according to embodiments.

For instance, FIG. 5 is a diagram of a sample pulse oximeter 501 according to embodiments. Sensor 501 can be part of the transducer, and be part of outside monitoring device 180. In the example of FIG. 5, sensor 501 is worn on the finger 582 of the patient, even though other locations are possible. A physiological input 521 can be rendered from sensor 501. Input 521 can be one or more blood oxygen saturation measurements.

As will be understood from the below, in embodiments, a WCD system makes shock/no shock determinations from multiple patient physiological parameters. This could mean that such determinations are made either from input 521 taken multiple times, or from such inputs from multiple locations taken together. Indeed, the one or more transducers could include two pulse oximeters that are applied to different parts of the patient's body, etc.

Combinations of transducers may also be used, and different parameters could be combined. For example, the analysis might include environmental parameters such as an accelerometer or impedance waveform signal. These parameters could be evaluated together with the ECG signal or instead of the ECG signal, so as to provide an overall indication of the patient's condition.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document.

Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 6:
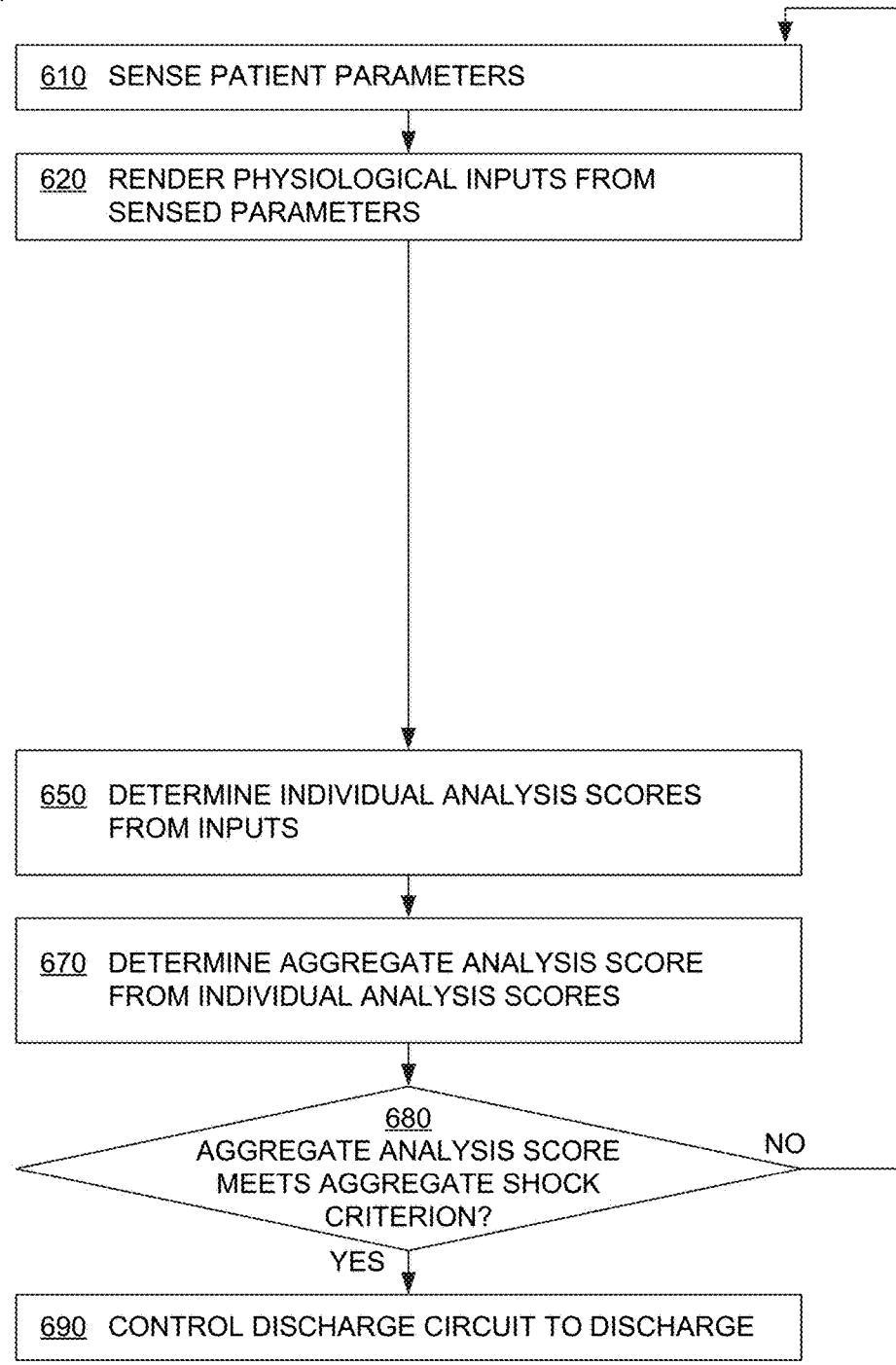
FIG. 6 is a flowchart for illustrating methods according to embodiments.
Figure 7:
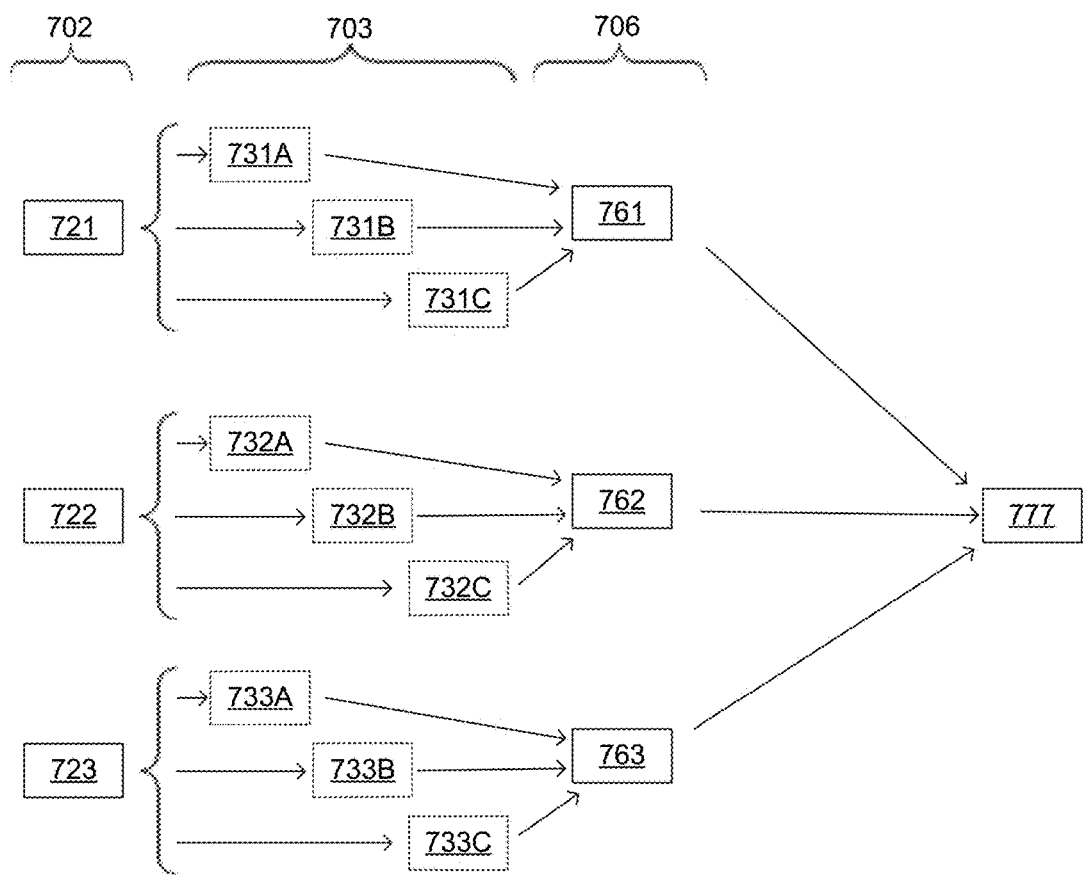
FIG. 7 is a sample diagram of how measurements can be aggregated for making determinations according to embodiments, and which can result from the flowchart of FIG. 6.

FIG. 6 shows a flowchart 600 for describing methods according to embodiments. FIG. 7 is a sample diagram of how measurements can be aggregated or grouped for making determinations according to embodiments. FIG. 7 can result from flowchart 600, or from other methods.

According to an operation 610 of FIG. 6, one or more patient parameters can be sensed by the one or more transducers. The sensing can be from different parts of the patient's body. In the case of ECG, the sensing can be from different vectors, which span different parts of the patient's body, even if these vectors share an electrode.

According to another operation 620, a plurality of physiological inputs can be rendered from the one or more patient parameters that are sensed at operation 610. In FIG. 7, a corresponding sample group 702 includes inputs 721, 722, 723.

According to another operation 650 of FIG. 6, a plurality of individual analysis scores can be determined from the physiological inputs of operation 620. In FIG. 7, a corresponding sample group 706 includes individual analysis scores 761, 762, 763, which are ultimately determined from inputs 721, 722, 723 respectively.

Operation 650 can be performed in a number of ways. In some embodiments, one or more of the individual analysis scores are binary and reflect whether or not one or more individual shock criteria are met. In other words, these individual analysis scores can either take the value of either "SHOCK" or "NO SHOCK", depending on whether or not one or more individual shock criteria are met. Such can be implemented, for example, by advice module 234, for each of the individual analysis scores.

In some embodiments, one or more of the individual analysis scores 761, 762, 763 include number values. Such values can reflect respective likelihoods that a shock is needed. This can be done without any of them reaching an individual decision.

In FIG. 7, a group 703 includes optional individual aspects detected from inputs 721, 722, 723. In this example, there are three aspects detected from each input. In particular, aspects 731A, 731B and 731C are detected from input 721; aspects 732A, 732B and 732C are detected from input 722; and aspects 733A, 733B and 733C are detected from input 723. Examples of such detected aspects (731A, 731B, 731C, 732A, 732B, 732C, 733A, 733B, 733C) are described later in this document. Each of the individual analysis scores 761, 762, 763 can be determined from the detected individual aspects. These optional individual aspects of group 703 are shown in FIG. 7 to better differentiate the methods of flowchart 600 from methods described later in this document. The individual aspects of group 703 could be aspects of an ECG waveform.

Other embodiments, however, do not need the individual aspects of group 703. For example, if inputs 721, 722, 723 are blood pressure measurements and/or blood oxygen saturation measurements, then such measurements may be used without detecting individual aspects from them.

Returning to FIG. 6, according to another operation 670, an aggregate analysis score may be determined from a plurality of individual analysis scores, such as those of operation 650. In FIG. 7, an aggregate analysis score 777 is determined from all three individual analysis scores 761, 762, 763. Some of the individual analysis scores, however, may be dropped if they are deemed unreliable, for example due to noise detected in the ECG measurement, etc.

Operation 670 can be performed in a number of ways. In embodiments where the individual analysis scores are binary ("SHOCK" or "NO SHOCK"), the aggregate analysis score can be determined by summing those of the individual analysis scores that have similar values. In other words, the individual analysis scores can be counted as votes to shock or to not shock. In some embodiments, the individual analysis scores include number values, and the aggregate analysis score is determined by summing the individual analysis scores, while applying equal or different weights to them.

According to another operation 680, it is determined whether or not the aggregate analysis score of operation 670 meets an aggregate shock criterion. This can be performed in a number of ways. For example, where the individual analysis scores are binary and the aggregate analysis score is determined like voting as above, the aggregate shock criterion of operation 680 can be a determination as to whether the aggregate analysis score of operation 670 exceeds a shock threshold.

A potential challenge with this approach, however, is that out of, say, three channels from three ECG vectors, only one might strongly point towards the proper recommendation, while two might weakly point towards the wrong recommendation. The first one may be outvoted. This risk can be mitigated, however, if the other sample approach is used, where the individual analysis scores include number values. In such cases the aggregate analysis score can be determined by summing the individual analysis scores as described above. Then the aggregate analysis score will be more immune to error, as it is being compared to a shock threshold.

If at operation 680 the answer is no, then execution may return to an earlier operation, such as operation 610. Plus, the discharge circuit can be controlled to not discharge the electrical charge through the patient for at least 27 min (minutes) from when the determination of operation 680 is performed.

If at operation 680 the answer is yes then, according to another operation 690, the discharge circuit can be controlled to discharge the electrical charge through the patient. This can happen within a convenient time, such as within 5 min from when the determination of operation 680 is performed. In the embodiments that use the shock threshold, the shock threshold can be, for example, 50%, and exceeding it can mean to shock instead of not shocking.

In some embodiments, operation 690 is performed the first time it is encountered. In other embodiments, operations performed previously to operation 690 (such as operation 680) are performed at least twice within a time interval (such as 4.5 minutes), and operation 690 takes place in response to the last time operation 680 is performed. Accordingly, at operation 690 the discharge circuit can be controlled to discharge the electrical charge through the patient within 5 min from when it is determined that the aggregate shock criterion is met, but only if: a) additional physiological inputs have been rendered from the one or more patient parameters that are sensed from the different parts of the patient's body, b) additional individual analysis scores have been determined from the additional physiological inputs, and c) characteristic analysis scores have been determined from at least some of the additional individual analysis scores for respective ones of the different parts of the patient's body. In such embodiments, the aggregate analysis score may have been determined from the characteristic analysis scores. An example is now described.

Figure 8:
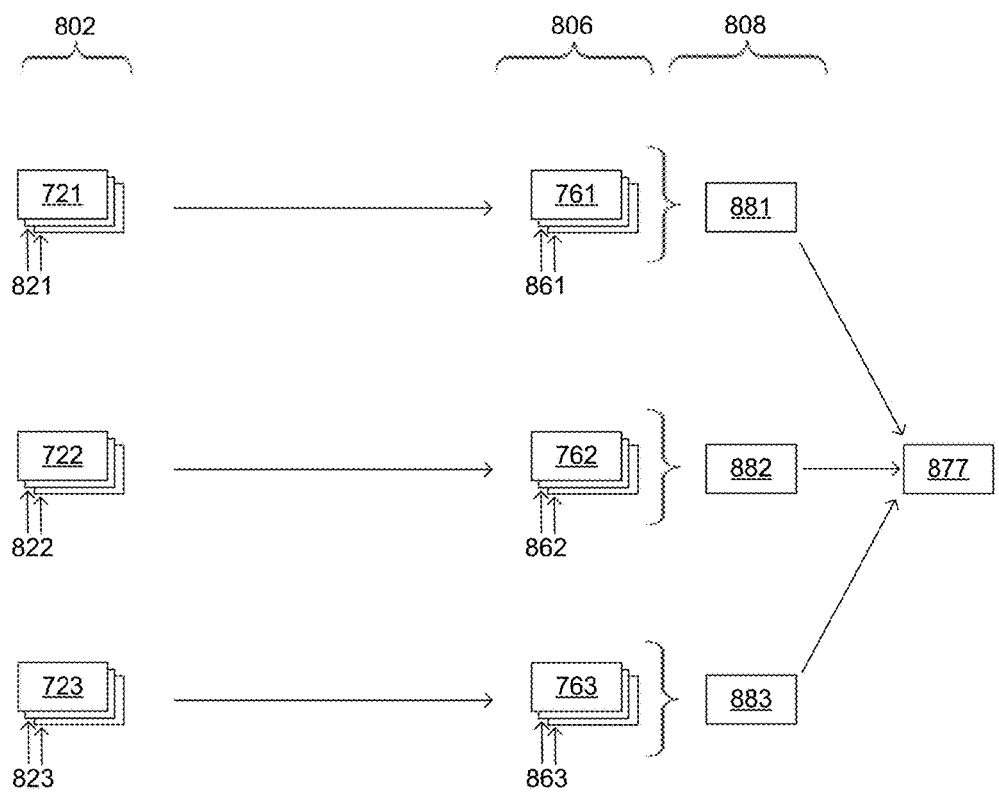
FIG. 8 is another sample diagram of how measurements can be aggregated for making determinations according to embodiments, and which can result from the flowchart of FIG. 6.

FIG. 8 is another sample diagram of how measurements can be aggregated for making determinations according to embodiments, where operations have been performed previously additional times, and gather additional data and results for a better informed shock/no shock decision. In particular, a group 802 shows physiological inputs 721, 821, 722, 822, 723, 823, which include not just one input 721, 722, 723 for each part of the body (first shown in FIG. 7), but also include additional physiological inputs 821, 822, 823, which may have been rendered from the one or more patient parameters that are sensed from the different parts of the patient's body.

Additionally, in FIG. 8 a group 806 shows individual analysis scores 761, 762, 763, plus additional individual analysis scores 861, 862, 863, which may have been determined from additional physiological inputs 821, 822, 823 respectively. In the example of FIG. 8, these additional individual analysis scores 861, 862, 863 are organized in sets to indicate that they are ultimately derived from the different parts of the body.

Moreover, in FIG. 8 a group 808 shows characteristic analysis scores 881, 882, 883. These may have been determined from at least some of individual analysis scores 761, 762, 763 and/or additional individual analysis scores 861, 862, 863, for respective ones of the different parts of the patient's body. Accordingly, characteristic analysis scores 881, 882, 883 can be characteristic of the part of the body. If the physiological inputs reflect ECG measurements, characteristic analysis scores 881, 882, 883 can be characteristic of the different ECG channels along different vectors. Characteristic analysis scores 881, 882, 883 can be more reliable than individual analysis scores 761, 762, 763, as they are accumulated over a longer time.

Furthermore, an aggregate analysis score which, in the example of FIG. 8 is indicated as 877, may have been determined from at least two of the characteristic analysis scores. Aggregate analysis score 877 may be used as described above for aggregate analysis score 777. It will be appreciated that more time is spent in arriving at aggregate analysis score 877 than in aggregate analysis score 777. A more reliable shock/no shock decision may be rendered.

Figure 9:
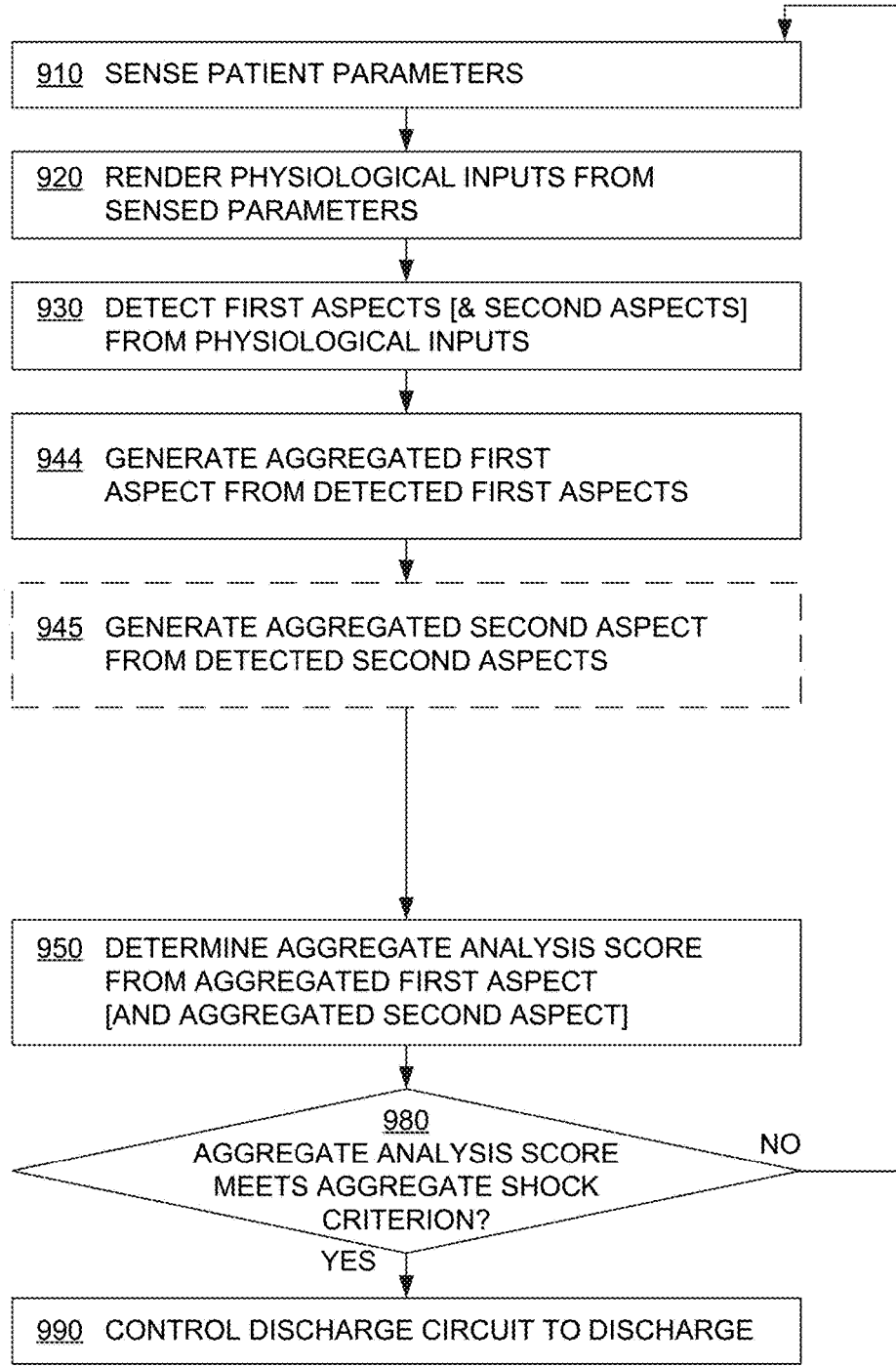
FIG. 9 is a flowchart for illustrating methods according to embodiments.
Figure 10:
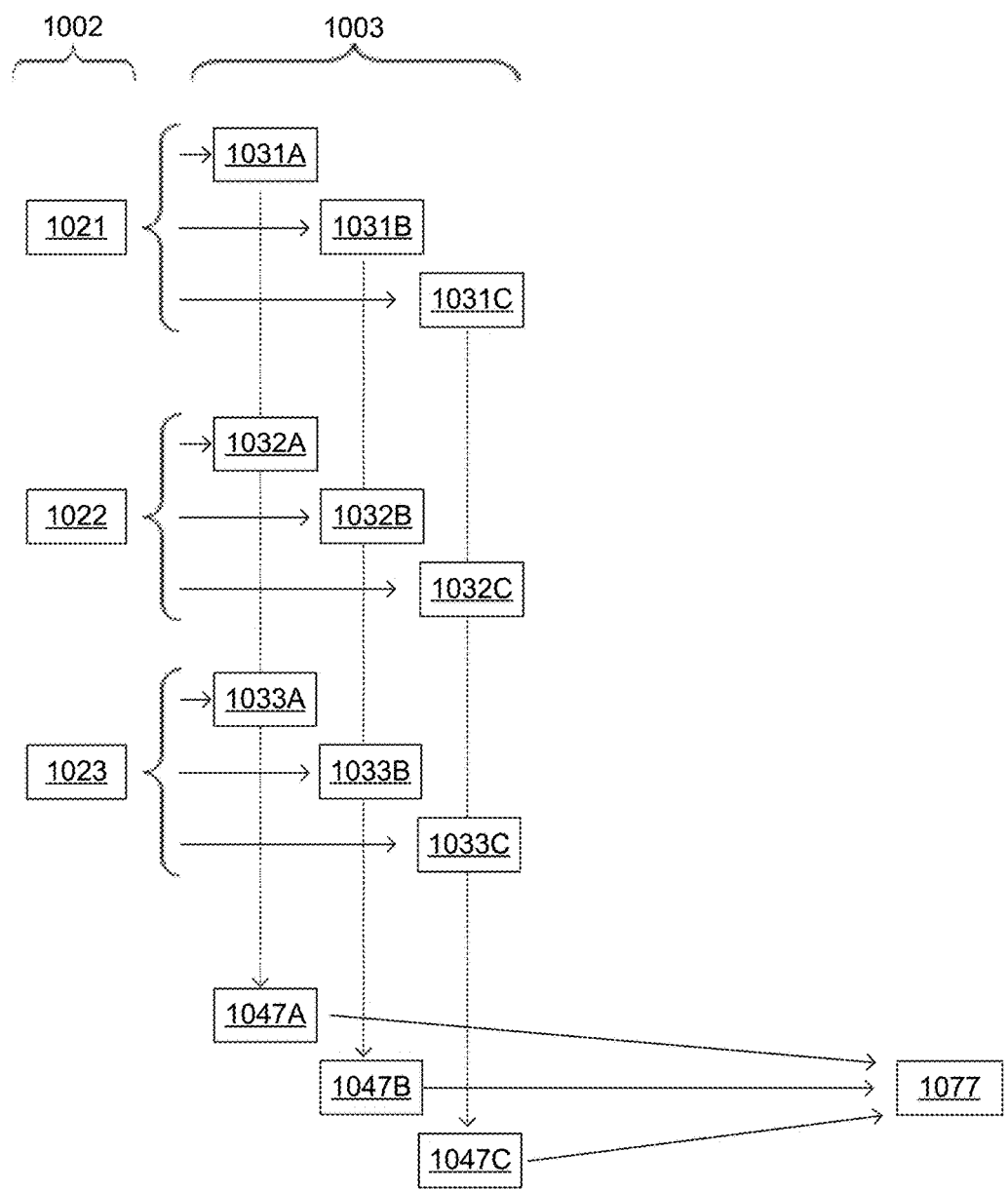
FIG. 10 is a sample diagram of how measurements can be aggregated for making determinations according to embodiments, and which can result from the flowchart of FIG. 9.

FIG. 9 shows a flowchart 900 for describing methods according to embodiments. FIG. 10 is a sample diagram of how measurements can be aggregated for making determinations according to embodiments. FIG. 10 can result from flowchart 900, or from other methods.

According to an operation 910 of FIG. 9, one or more patient parameters can be sensed by the one or more transducers. The sensing can be from different parts of the patient's body.

According to another operation 920, a plurality of physiological inputs can be rendered from the one or more patient parameters that are sensed at operation 910. In FIG. 10, a corresponding sample group 1002 includes inputs 1021, 1022, 1023.

According to another operation 930, first aspects may be detected from each of at least some of the physiological inputs. In some embodiments, also second aspects are detected from each of at least some of the physiological inputs. In some embodiments, third aspects are further detected from each of at least some of the physiological inputs. In FIG. 10, a group 1003 includes individual aspects detected from inputs 1021, 1022, 1023. In this example, there are three aspects detected from each input. In particular, aspects 1031A, 1031B and 1031C are detected from input 1021; aspects 1032A, 1032B and 1032C are detected from input 1022; and aspects 1033A, 1033B and 1033C are detected from input 1023. The individual aspects of group 1003 could be aspects of an ECG waveform.

The detected aspects can be for subgroups of features similar to each other. For instance, the detected first aspects can be for a subgroup of first features that are similar to each other, the detected second aspects can be for another subgroup of second features that are similar to each other, and so on. For example, if the physiological inputs reflect ECG measurements, the detected aspects of the ECG measurements can be about values the heart rate, the amplitude of the ECG waveform or a feature of it, such as a QRS complex, a width of such QRS complex that is measured at a suitable location of the ECG waveform such as the base of the QRS complex, QRS organization, and so on. Examples of these detected aspects are now described individually in more detail, while sample values for them are provided later in this document.

The detected first aspects may include respective values for a heart rate. Heart rate may be very probative as to whether a patient should be shocked or not. Heart rate may be determined by detecting QRS complexes and measuring the time interval between complexes, or by using Fast Fourier Transforms, autocorrelation methods, etc.

The detected first aspects may include respective values for a width of one or more QRS complexes, a quantity that is often called "QRS width". QRS width may be determined by measuring the time required to return to baseline, for detected QRS complexes. QRS width could also be determined approximately from a duty cycle of an ECG signal.

The detected first aspects may include respective values for a measure of QRS organization. QRS organization may be determined by examining detected QRS complexes for similarities between them. Similarity can be assessed in a number of ways, for example by looking at a Root Mean Square difference between two QRS complexes, cross-correlating QRS complexes, etc.

The detected aspects can further include values for features of these inputs. In the immediately above example, aspects of the ECG measurements can include values for a heart rate, an amplitude of the waveform, a width of the QRS complex, and so on.

According to another operation 944, an aggregated first aspect is generated from at least two of the detected first aspects. In the example of FIG. 10, an aggregated first aspect 1047A is generated from detected first aspects 1031A, 1032A, 1033A. There is a number of ways of generating this aggregated first aspect 1047A, which are described later in this document.

Returning to FIG. 9, according to another, optional operation 945, an aggregated second aspect is generated from at least one of the detected second aspects. In the example of FIG. 10, an aggregated second aspect 1047B is generated from detected second aspects 1031B, 1032B, 1033B. Operation 945 is optional because a decision can be based on a single aspect (the first aspect) which can be, for example the heart rate.

According to another, optional operation, an aggregated third aspect is generated from at least one of the detected third aspects. In the example of FIG. 10, an aggregated third aspect 1047C is generated from detected third aspects 1031C, 1032C, 1033C.

Generating the aggregated aspects is now described in more detail. This portion of the description is the same whether it applies to the aggregated first, second, or third aspect.

In some embodiments, one of the aggregated aspects is generated from a first statistic of values of at least two of the corresponding individual detected aspects. For example, the aggregated aspect can be generated by averaging values of at least two of the corresponding detected aspects.

It is not necessary that all detected aspects will be used. Some may be discarded as clearly erroneous, for instance if their values are outliers. For example, the aggregated aspect can be generated by averaging values of at least two aspects, after the highest and lowest values are removed; such removal can help guard against outliers. Or, the aggregated aspect can be generated by choosing a median value of values of at least three of the detected corresponding aspects. Choosing a median value requires less processing than averaging, and may implicitly guard against outliers.

In some embodiments, some of the detected aspects may have values that appear valid, yet these are discarded in view of the other available values for the same aspect. For example, the detected aspects may include at least two values for a heart rate, and the aggregated corresponding aspect can be generated by choosing a minimum value of the at least two values for the heart rate. For another example, the detected aspects may include at least two values for a width of one or more QRS complexes, and the aggregated corresponding aspect can be generated by choosing a maximum value of the at least two values for the width of the one or more QRS complexes.

Returning to FIG. 9, according to another operation 950, an aggregate analysis score may be determined from the aggregated first aspect of operation 944. The aggregate analysis score may even be a value of the aggregated first aspect of operation 944 itself.

For example, this first aspect could be the patient's heart rate, as mentioned above. Since the patient has only one heart, the detected heart rate should be the same from each channel. Regardless, this detection can be confounded by noise, which can be different in each channel; moreover, for some rhythms, some vectors might be easier to interpret than others.

One way of aggregating heart rate across channels is to look for agreement in the heart rates detected by the available channels. With multiple channels, agreement is unlikely to happen randomly. If multiple channels agree then that value is probably correct.

If there is no agreement among the channels, deciding the heart rate can become harder. One could take the average, the median, the maximum, the minimum, or other statistical values. But all of these methods have limitations. For example, if you get heart rate values of 80, 90, and 400, the average would be 190 even though it is likely the person's heart rate is in the 80-90 range. Accordingly, outliers can be first rejected, as per the above.

One may also look for agreement within channels. For example, a channel with less R-R interval variation likely has less noise than one with more variation. This is true even for rhythms that are expected to have R-R variation, like VF and atrial fibrillation. Also, QRS amplitude consistency is another indicator of channel "goodness."

Channels can be discounted according to a noise assessment. Common methods of noise assessment include looking for low-frequency noise by baseline shift, looking for amplitudes outside of the expected range, or looking for high-frequency noise with an FFT or zero crossings. Channels derived from electrodes that are measured to be high-impedance could be discounted.

For another example, this first aspect could be the patient's QRS width. Channel selection for QRS width will likely use a different method than heart rate. Unlike with detected heart rate values, QRS width values are not expected to be consistent across channels. QRS width values often vary across channels, so averaging over channels would probably not be the best plan. Clinically, the channel with the widest width is probably the one of interest, one method is to simply choose the channel that measures the widest width. However, the measured values could be confounded by noise. The noise detection techniques measured above can also be applied to the QRS width channel selection. In some embodiments, the channel(s) used to derive the heart rate might be different from the channel used to derive the QRS width.

In some embodiments, the aggregate analysis score of operation 950 is determined also from the aggregated second aspect of operation 945. In addition, if third aspects have been detected as mentioned, and an aggregated third aspect has been generated from them, then the aggregate analysis score can be determined also from the aggregated third aspect. For example, in FIG. 10 an aggregate analysis score 1077 is determined from aggregated first aspect 1047A, aggregated second aspect 1047B, and aggregated third aspect 1047C.

Operation 950 can be performed in a number of ways. In some embodiments, the aggregate analysis score includes a vector of logical values as to whether its aspects meet certain intermediate criteria, or as to whether values of these aspects meet some thresholds. In some embodiments, the aggregate analysis score includes a vector of numerical values for its aspects, and/or combinations of these numerical values. For example, the aggregate analysis score may include a single numerical parameter, which can be called shock index. The Shock Index can be given by an equation like SI=HRCoeff*HR+ACoeff*A+QRSWCoeff*QRSW, where HR, A and QRSW are the above sample three aspects of heart rate, amplitude and QRS width, and which are multiplied by suitable coefficients.

It will be recognized that similar considerations could be applied for determining each of the previously discussed individual analysis scores 761, 762, 763 of FIG. 7, for the cases of ECG. A difference, however, is that the individual components of aggregate analysis score 1077 are more robustly computed from aggregated aspects 1047A, 1047B, and 1047C, because the conversion from continuous variables to a binary shock/no shock determination is deferred to a later operation in the computation, and thus extracts more value from the available data in performing the shock/no shock recommendation.

Returning to FIG. 9, according to another operation 980, it is determined whether or not the aggregate analysis score of operation 950 meets an aggregate shock criterion. This can be performed in a number of ways, often in conjunction with how operation 950 is implemented. For example, any one or more logical values in a vector may meet the aggregate shock criterion. The aggregate shock criterion could use an AND function, for example requiring a heart rate greater than a maximum (e.g. HR>170 beats per minute), an amplitude greater than a maximum (e.g. A>200 µV), and a QRS width greater than a maximum (e.g. QRSW>120 msec). Or, the aggregate shock criterion can be met if a numerical condition is met, such as by numerical values for its aspects in a vector or the Shock Index, etc. Operation 980 can be implemented, for example, by advice module 234.

Still in FIG. 9, if at operation 980 the answer is no, then execution may return to an earlier operation, such as operation 910. Plus, the discharge circuit can be controlled to not discharge the electrical charge through the patient for at least 19 min from when the determination of operation 980 is performed.

If at operation 980 the answer is yes then, according to another operation 990, the discharge circuit can be controlled to discharge the electrical charge through the patient. This can happen within a convenient time, such as within 6 min from when the determination of operation 980 is performed. In the embodiments that use the shock threshold, the shock threshold can be, for example, 50%, and exceeding it can mean to shock.

In some embodiments, operation 990 is performed the first time it is encountered. In other embodiments, operations performed previously to operation 990 (such as operation 980) are performed at least twice within a time interval (such as 4.7 minutes), and operation 990 takes place in response to the last time operation 980 is performed. Accordingly, at operation 990 the discharge circuit can be controlled to discharge the electrical charge through the patient within 6 min from when it is determined that the aggregate shock criterion is met, but only if: a) additional physiological inputs have been rendered from the one or more patient parameters that are sensed from the different parts of the patient's body, b) additional first aspects and additional second aspects have been detected from each of at least some of the additional physiological inputs, c) a plurality of characteristic first aspects have been determined from at least some of the additional detected first aspects for respective ones of the different parts of the patient's body, and d) a plurality of characteristic second aspects have been determined from at least some of the additional detected second aspects for respective ones of the different parts of the patient's body. In such embodiments, the aggregated first aspect may have been determined from at least two of the characteristic first aspects, and the aggregated second aspect may have been determined from at least two of the characteristic second aspects. An example is now described.

Figure 11:
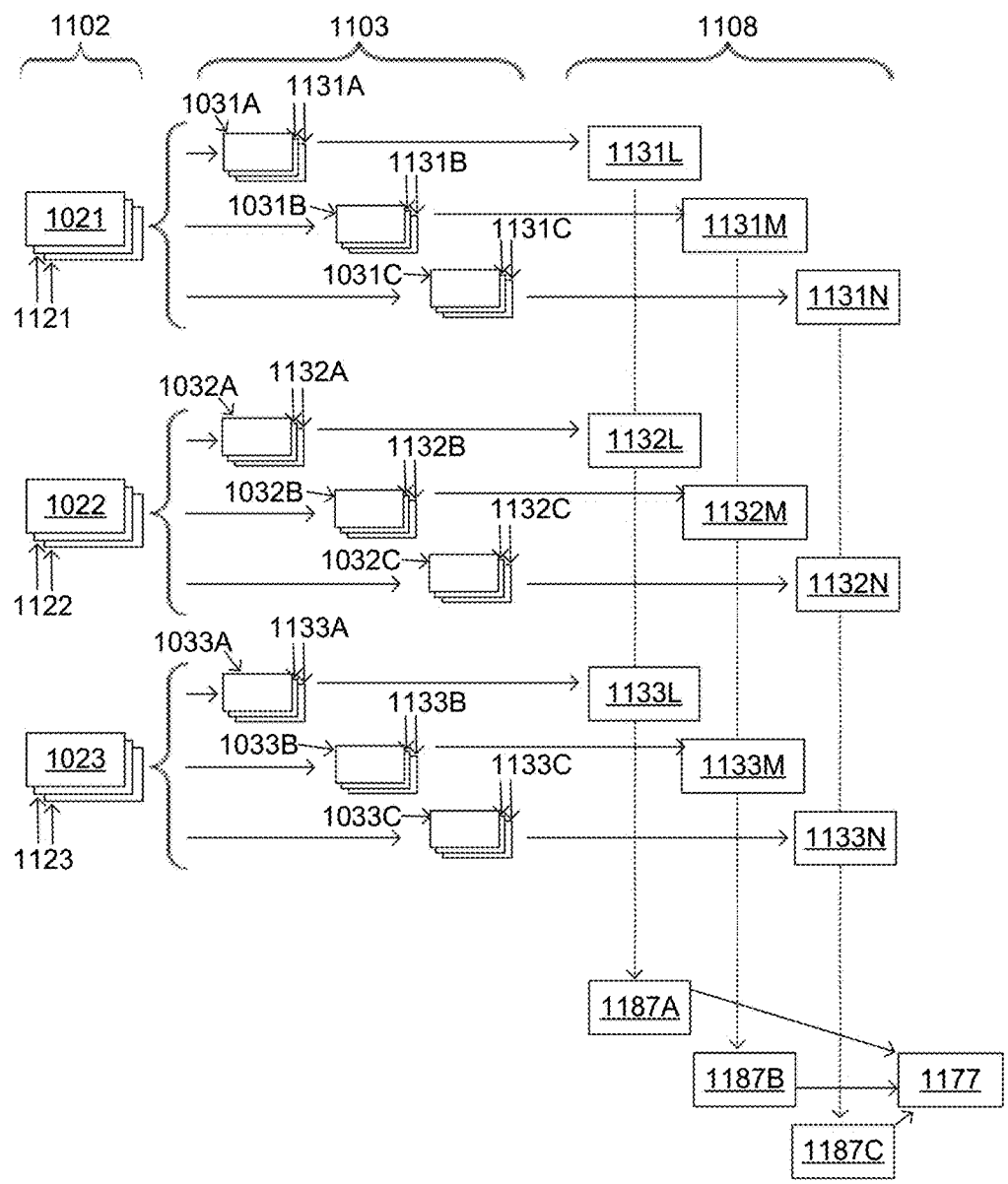
FIG. 11 is another sample diagram of how measurements can be aggregated for making determinations according to embodiments, and which can result from the flowchart of FIG. 9.

FIG. 11 is another sample diagram of how measurements can be aggregated for making determinations according to embodiments, where operations have been performed previously additional times, and gather additional data and results for a better informed shock/no shock decision. In particular, a group 1102 shows physiological inputs 1021, 1121, 1022, 1122, 1023, 1123, which include not just one input 1021, 1022, 1023 for each part of the body (first shown in FIG. 10), but also include additional physiological inputs 1121, 1122, 1123, which may have been rendered from the one or more patient parameters that are sensed from the different parts of the patient's body.

Moreover, in FIG. 11 a group 1103 shows detected first aspects 1031A, 1031B, 1031C, detected second aspects 1032A, 1032B, 1032C, and detected third aspects 1033A, 1033B, 1033C. Group 1103 also shows additional detected first aspects 1131A, 1131B, 1131C, additional detected second aspects 1132A, 1132B, 1132C, and additional detected third aspects 1133A, 1133B, 1133C, any and all of which may have been detected from each of at least some of additional physiological inputs 1121, 1122, 1123.

Furthermore, in FIG. 11 a group 1108 shows characteristic first aspects 1131L, 1132L, 1133L, characteristic second aspects 1131M, 1132M, 1133M, and characteristic third aspects 1131N, 1132N, 1133N. Characteristic first aspects 1131L, 1132L, 1133L may have been determined from at least two of additional detected first aspects 1131A, 1131B, 1131C for respective ones of the different parts of the patient's body. Characteristic second aspects 1131M, 1132M, 1133M may have been determined from at least two of additional detected second aspects 1132A, 1132B, 1132C for respective ones of the different parts of the patient's body. Characteristic third aspects 1131N, 1132N, 1133MN may have been determined from at least two of additional detected third aspects 1133A, 1133B, 1133C for respective ones of the different parts of the patient's body.

The characteristic first, second and third aspects may be determined in a number of ways. In many embodiments, one of these is determined as a value from a statistic of values of the additional detected first aspects from which it is determined. The statistic can be an average, a maximum, a minimum and so on.

In such embodiments, aggregated first aspect 1187A may have been determined from at least two of characteristic first aspects 1131L, 1132L 1133L. In addition, aggregated second aspect 1187B may have been determined from at least two of characteristic second aspects 1131M, 1132M, 1133M. Moreover, aggregated third aspect 1187C may have been determined from at least two of characteristic second aspects 1131N, 1132N, 1133N. Aggregated first, second and third aspects 1187A, 1187B, 1187C may be used instead of aggregated first, second and third aspects 1047A, 1047B, 1047C. It will be appreciated that more time is spent in arriving at aggregate analysis score 1177 than in aggregate analysis score 1077. A more reliable shock/no shock decision may be rendered.

In some embodiments, at least some of the detected aspects of groups 1103, 1108 may be retained over time, for example using memory 238. This could help where the shock recommendation may change over time. In such embodiments, the above-described aggregation can be performed from filtered values of corresponding aspects over time, to determine the corresponding values. For example, at least some of the detected first aspects, second aspects, etc., plus the additional detected first aspects, etc. can be filtered over time. Or, when the aggregate analysis score is determined also from the aggregated second aspect, an additional aggregate analysis score can be determined after the original aggregate analysis score is determined, the original aggregate analysis score and the additional aggregate analysis score can be filtered over time, and the aggregate analysis score can be updated by the filtering, before it is determined whether or not the aggregate shock criterion is met. For example, one could take individual heart rate and QRS width values, determine a shock result, and aggregate the shock results over time.

Filtering can be performed conventionally, or by a suitable numerical combination of values. When a new value is received the older value can discarded, and the new value can take its place in a table. The filter could be either an IIR or an FIR filter. A filter may be chosen to give a good combination of step response and noise rejection. A FIR filter could be implemented using a stream of ECG data, while an IIR filter also requires a history of the filtered values. The transient response of an FIR filter may be better behaved than an IIR filter, but the IIR filter will have more noise attenuation for a given number of taps. An example FIR filter might use a Hamming window to determine the coefficients, while an example IIR filter would be a Butterworth filter.

A median filter may also be used to combine values over time. A median filter has the advantage that it is substantially insensitive to outliers. A single median filter could be used for an entire memory block. Alternatively, median filters of different lengths may be combined to give a single value with the desired time response. For example, the output of a 60 second median filter may be combined with a 15 second median filter and a 5 second median filter using linear weighting factors. Such a combination could be designed to give a relatively fast time response while still gaining some of the noise rejection from a longer memory.

History values could be flushed and replaced with new values upon certain predetermined events. For example, after delivering a shock it might be reasonably assumed that the patient's rhythm has changed, in which case the values in memory could be replaced with new measurements before they are utilized.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable cardioverter defibrillator ("WCD") system, comprising:
   a support structure configured to be worn by a patient;
   a power source;
   an energy storage module configured to be charged from the power source so as to store an electrical charge;

a discharge circuit;
one or more transducers configured to render a plurality of physiological inputs from one or more patient parameters that are sensed from different parts of the patient's body; and
a processor configured to:
  determine a plurality of individual analysis scores from the physiological inputs,
  determine an aggregate analysis score from a plurality of the individual analysis scores,
  determine whether or not the aggregate analysis score meets an aggregate shock criterion, and
  responsive to determining that the aggregate shock criterion is met, control the discharge circuit to discharge the stored electrical charge through the patient within 5 min from when it is determined that the aggregate shock criterion is met, else responsive to determining that the aggregate shock criterion is not met, control the discharge circuit to not discharge the stored electrical charge through the patient for at least 27 min from when it is determined that the aggregate shock criterion is not met.

2. The WCD system of claim 1, in which
the one or more transducers include at least three Electrocardiogram (ECG) electrodes configured to contact the patient so as to define a plurality of vectors, and
in which the patient parameters are electrical patient physiological signals measured along the vectors,
the transducer further includes a measurement circuit, and
the physiological inputs reflect ECG measurements measured along the vectors.

3. The WCD system of claim 1, in which
the patient parameter is a blood pressure,
the one or more transducers include a blood pressure sensor, and
the physiological inputs include blood pressure measurements.

4. The WCD system of claim 1, in which
the patient parameter is a blood pressure,
the one or more transducers include two blood pressure sensors configured to render physiological inputs from different parts of the patient's body, and
the physiological inputs include blood pressure measurements.

5. The WCD system of claim 1, in which
the patient parameter is a blood oxygen saturation,
the one or more transducers include a pulse oximeter, and
the physiological inputs include blood oxygen saturation measurements.

6. The WCD system of claim 1, in which
the patient parameter is a blood oxygen saturation,
the one or more transducers include two pulse oximeters configured to render physiological inputs from different parts of the patient's body, and
the physiological inputs include blood oxygen saturation measurements.

7. The WCD system of claim 1, in which
one or more of the individual analysis scores are binary and reflect whether or not one or more individual shock criteria are met.

8. The WCD system of claim 1, in which
one or more of the individual analysis scores include number values that reflect respective likelihoods that a shock is needed.

9. The WCD system of claim 1, in which
the individual analysis scores are binary, and
the aggregate analysis score is determined by summing those of the individual analysis scores that have similar values.

10. The WCD system of claim 1, in which
the individual analysis scores include number values, and
the aggregate analysis score is determined by summing the individual analysis scores.

11. The WCD system of claim 1, in which
the individual analysis scores include number values, and
the aggregate analysis score is determined by summing the individual analysis scores while applying different weights to the individual analysis scores.

12. The WCD system of claim 1, in which
the discharge circuit is controlled to discharge the electrical charge through the patient within 5 min from when it is determined that the aggregate shock criterion is met, but only if:
additional physiological inputs have been rendered from the one or more patient parameters that are sensed from the different parts of the patient's body,
additional individual analysis scores have been determined from the additional physiological inputs,
characteristic analysis scores have been determined from at least some of the additional individual analysis scores for respective ones of the different parts of the patient's body, and
in which the aggregate analysis score has been determined from at least two of the characteristic analysis scores.

13. A non-transitory computer-readable storage medium storing one or more programs which, when executed by at least one processor of a wearable cardioverter defibrillator ("WCD") system, the WCD system including a support structure configured to be worn by a patient, a power source, an energy storage module configured to be charged from the power source so as to store an electrical charge, a discharge circuit and one or more transducers, these one or more programs result in operations comprising:
  sensing one or more patient parameters from different parts of the patient's body by the one or more transducers;
  rendering a plurality of physiological inputs from the sensed one or more patient parameters;
  determining a plurality of individual analysis scores from the physiological inputs;
  determining an aggregate analysis score from a plurality of the individual analysis scores;
  determining whether or not the aggregate analysis score meets an aggregate shock criterion; and
  responsive to determining that the aggregate shock criterion is met, controlling the discharge circuit to discharge the stored electrical charge through the patient within 5 min from when it is determined that the aggregate shock criterion is met, else responsive to determining that the aggregate shock criterion is not met, controlling the discharge circuit to not discharge the stored electrical charge through the patient for at least 27 min from when it is determined that the aggregate shock criterion is not met.

14. The medium of claim 13, in which
one or more of the individual analysis scores are binary and reflect whether or not one or more individual shock criteria are met.

15. The medium of claim 13, in which
one or more of the individual analysis scores include number values that reflect respective likelihoods that a shock is needed.

16. The medium of claim 13, in which
the individual analysis scores are binary, and
the aggregate analysis score is determined by summing those of the individual analysis scores that have similar values.

17. The medium of claim 13, in which
the individual analysis scores include number values, and
the aggregate analysis score is determined by summing the individual analysis scores.

18. The medium of claim 13, in which
the individual analysis scores include number values, and
the aggregate analysis score is determined by summing the individual analysis scores while applying different weights to the individual analysis scores.

19. The medium of claim 13, in which
the discharge circuit is controlled to discharge the electrical charge through the patient within 5 min from when it is determined that the aggregate shock criterion is met, but only if:
additional physiological inputs have been rendered from the one or more patient parameters that are sensed from the different parts of the patient's body,
additional individual analysis scores have been determined from the additional physiological inputs,
characteristic analysis scores have been determined from at least some of the additional individual analysis scores for respective ones of the different parts of the patient's body, and
in which the aggregate analysis score has been determined from at least two of the characteristic analysis scores.

20. A method for a wearable cardioverter defibrillator ("WCD") system, the WCD system including a support structure configured to be worn by a patient, a power source, an energy storage module configured to be charged from the power source so as to store an electrical charge, a discharge circuit and one or more transducers, the method comprising:
sensing one or more patient parameters from different parts of the patient's body by the one or more transducers;
rendering a plurality of physiological inputs from the sensed one or more patient parameters;
determining a plurality of individual analysis scores from the physiological inputs;
determining an aggregate analysis score from a plurality of the individual analysis scores;
determining whether or not the aggregate analysis score meets an aggregate shock criterion; and
responsive to determining that the aggregate shock criterion is met, controlling the discharge circuit to discharge the stored electrical charge through the patient within 5 min from when it is determined that the aggregate shock criterion is met, else responsive to determining that the aggregate shock criterion is not met, controlling the discharge circuit to not discharge the stored electrical charge through the patient for at least 27 min from when it is determined that the aggregate shock criterion is not met.

21. The method of claim 20, in which
one or more of the individual analysis scores are binary and reflect whether or not one or more individual shock criteria are met.

22. The method of claim 20, in which
one or more of the individual analysis scores include number values that reflect respective likelihoods that a shock is needed.

23. The method of claim 20, in which
the individual analysis scores are binary, and
the aggregate analysis score is determined by summing those of the individual analysis scores that have similar values.

24. The method of claim 20, in which
the individual analysis scores include number values, and
the aggregate analysis score is determined by summing the individual analysis scores.

25. The method of claim 20, in which
the individual analysis scores include number values, and
the aggregate analysis score is determined by summing the individual analysis scores while applying different weights to the individual analysis scores.

26. The method of claim 20, in which
the discharge circuit is controlled to discharge the electrical charge through the patient within 5 min from when it is determined that the aggregate shock criterion is met, but only if:
additional physiological inputs have been rendered from the one or more patient parameters that are sensed from the different parts of the patient's body,
additional individual analysis scores have been determined from the additional physiological inputs,
characteristic analysis scores have been determined from at least some of the additional individual analysis scores for respective ones of the different parts of the patient's body, and
in which the aggregate analysis score has been determined from at least two of the characteristic analysis scores.

* * * * *